United States Patent
Sahney et al.

(10) Patent No.: US 9,155,454 B2
(45) Date of Patent: Oct. 13, 2015

(54) HYSTEROSCOPIC SYSTEM

(75) Inventors: Mira Sahney, Boston, MA (US); Cemal Shener-Irmakoglu, Woburn, MA (US)

(73) Assignee: Smith & Nephew, Inc., Memphis, TN (US)

( * ) Notice: Subject to any disclaimer, the term of this patent is extended or adjusted under 35 U.S.C. 154(b) by 385 days.

(21) Appl. No.: 12/892,355

(22) Filed: Sep. 28, 2010

(65) Prior Publication Data

US 2012/0078038 A1  Mar. 29, 2012

(51) Int. Cl.
| | |
|---|---|
| *A61B 1/00* | (2006.01) |
| *A61B 1/12* | (2006.01) |
| *A61M 5/00* | (2006.01) |
| *A61B 17/32* | (2006.01) |
| *A61B 1/015* | (2006.01) |
| *A61B 17/34* | (2006.01) |
| *A61B 1/018* | (2006.01) |
| *A61B 1/307* | (2006.01) |
| *A61B 1/303* | (2006.01) |

(52) U.S. Cl.
CPC .............. *A61B 1/015* (2013.01); *A61B 1/00135* (2013.01); *A61B 1/018* (2013.01); *A61B 1/307* (2013.01); *A61B 17/32002* (2013.01); *A61B 17/3421* (2013.01); *A61B 1/303* (2013.01); *A61B 2017/320024* (2013.01); *A61B 2017/320028* (2013.01); *A61B 2217/007* (2013.01)

(58) Field of Classification Search
CPC . A61M 25/007; A61B 1/015; A61B 1/00135; A61B 17/3421; A61B 2017/32002; A61B 2017/320024; A61B 2017/320028

USPC ......... 600/104, 128, 129, 130, 153, 156, 121; 606/170; 604/264

See application file for complete search history.

(56) References Cited

U.S. PATENT DOCUMENTS

| | | | |
|---|---|---|---|
| 1,585,934 | A | 5/1926 | Muir |
| 1,666,332 | A | 4/1928 | Hirsch |
| 1,831,786 | A | 11/1931 | Duncan |
| 2,708,437 | A | 5/1955 | Hutchins et al. |
| 3,297,022 | A | 1/1967 | Wallace |
| 3,686,706 | A | 8/1972 | Finley |
| 3,734,099 | A | 5/1973 | Bender et al. |

(Continued)

FOREIGN PATENT DOCUMENTS

| | | |
|---|---|---|
| DE | 3339322 A1 | 5/1984 |
| DE | 3206381 C2 | 7/1986 |

(Continued)

OTHER PUBLICATIONS

International search report and written opinion regarding International patent application PCT/US2011/053753 mailed on Dec. 20, 2011.

(Continued)

*Primary Examiner* — Anhtuan T Nguyen
*Assistant Examiner* — Aaron B Fairchild
(74) *Attorney, Agent, or Firm* — Nixon Peabody LLP

(57) ABSTRACT

A hysteroscopy system includes a scope having an internal channel, a sheath removably coupled to the scope, and an outflow channel. The sheath has a distal flange extending internally towards an outer surface of the scope. The outflow channel is formed between an inner surface of the sheath and an outer surface of the scope. The distal flange forms a distal end of the outflow channel and is generally located between the scope and the sheath.

16 Claims, 8 Drawing Sheets

(56) References Cited

U.S. PATENT DOCUMENTS

| | | | |
|---|---|---|---|
| 3,791,379 | A | 2/1974 | Storz |
| 3,812,855 | A | 5/1974 | Banko |
| 3,850,162 | A | 11/1974 | Iglesias |
| 3,945,375 | A | 3/1976 | Banko |
| 3,980,252 | A | 9/1976 | Tae |
| 3,995,619 | A | 12/1976 | Glatzer |
| 3,996,921 | A | 12/1976 | Neuwirth |
| 4,011,869 | A | 3/1977 | Seiler, Jr. |
| 4,108,182 | A | 8/1978 | Hartman et al. |
| 4,146,405 | A | 3/1979 | Timmer et al. |
| 4,198,958 | A | 4/1980 | Utsugi |
| 4,203,444 | A | 5/1980 | Bonnell et al. |
| 4,210,146 | A | 7/1980 | Banko |
| 4,246,902 | A | 1/1981 | Martinez |
| 4,247,180 | A | 1/1981 | Norris |
| 4,258,721 | A | 3/1981 | Parent |
| 4,261,346 | A | 4/1981 | Wettermann |
| 4,294,234 | A | 10/1981 | Matsuo |
| 4,316,465 | A | 2/1982 | Dotson, Jr. |
| 4,369,768 | A | 1/1983 | Vukovic |
| 4,392,485 | A | 7/1983 | Hiltebrandt |
| 4,414,962 | A | 11/1983 | Carson |
| 4,449,538 | A | 5/1984 | Corbitt et al. |
| 4,493,698 | A | 1/1985 | Wang et al. |
| 4,517,977 | A | 5/1985 | Frost |
| 4,543,965 | A | 10/1985 | Pack et al. |
| 4,567,880 | A | 2/1986 | Goodman |
| 4,589,414 | A | 5/1986 | Yoshida et al. |
| 4,601,290 | A | 7/1986 | Effron et al. |
| 4,606,330 | A | 8/1986 | Bonnet |
| 4,630,598 | A | 12/1986 | Bonnet |
| 4,644,952 | A | 2/1987 | Patipa et al. |
| 4,649,919 | A | 3/1987 | Thimsen et al. |
| 4,700,694 | A | 10/1987 | Shishido |
| 4,706,656 | A | 11/1987 | Kuboto |
| 4,718,291 | A | 1/1988 | Wood et al. |
| 4,737,142 | A | 4/1988 | Heckele |
| 4,749,376 | A | 6/1988 | Kensey et al. |
| 4,756,309 | A | 7/1988 | Sachse et al. |
| 4,819,635 | A | 4/1989 | Shapiro |
| 4,844,064 | A | 7/1989 | Thimsen et al. |
| 4,850,354 | A | 7/1989 | McGurk-Burleson et al. |
| 4,856,919 | A | 8/1989 | Takeuchi et al. |
| 4,867,157 | A | 9/1989 | McGurk-Burleson et al. |
| 4,924,851 | A | 5/1990 | Ognier et al. |
| 4,940,061 | A | 7/1990 | Terwilliger et al. |
| 4,950,278 | A | 8/1990 | Sachse et al. |
| 4,955,882 | A | 9/1990 | Hakky |
| 4,986,827 | A | 1/1991 | Akkas et al. |
| 4,998,527 | A | 3/1991 | Meyer |
| 4,998,914 | A | 3/1991 | Wiest et al. |
| 5,007,917 | A | 4/1991 | Evans |
| 5,027,792 | A | 7/1991 | Meyer |
| 5,037,386 | A | 8/1991 | Marcus et al. |
| 5,105,800 | A | 4/1992 | Takahashi et al. |
| 5,106,364 | A | 4/1992 | Hayafuji et al. |
| 5,112,299 | A | 5/1992 | Pascaloff |
| 5,116,868 | A | 5/1992 | Chen et al. |
| 5,125,910 | A | 6/1992 | Freitas |
| 5,133,713 | A | 7/1992 | Huang et al. |
| 5,152,744 | A | 10/1992 | Krause et al. |
| 5,158,553 | A | 10/1992 | Berry et al. |
| 5,163,433 | A | 11/1992 | Kagawa et al. |
| 5,169,397 | A | 12/1992 | Sakashita et al. |
| 5,176,677 | A | 1/1993 | Wuchinich |
| 5,195,541 | A | 3/1993 | Obenchain |
| 5,226,910 | A | 7/1993 | Kajiyama et al. |
| 5,244,459 | A | 9/1993 | Hill |
| 5,254,117 | A | 10/1993 | Rigby et al. |
| 5,269,785 | A | 12/1993 | Bonutti |
| 5,270,622 | A | 12/1993 | Krause |
| 5,275,609 | A | 1/1994 | Pingleton et al. |
| 5,288,290 | A | 2/1994 | Brody |
| 5,304,118 | A | 4/1994 | Trese et al. |
| 5,312,399 | A | 5/1994 | Hakky et al. |
| 5,312,425 | A | 5/1994 | Evans et al. |
| 5,312,430 | A | 5/1994 | Rosenbluth et al. |
| 5,320,091 | A | 6/1994 | Grossi et al. |
| 5,347,992 | A | 9/1994 | Pearlman et al. |
| 5,350,390 | A | 9/1994 | Sher |
| 5,364,395 | A | 11/1994 | West, Jr. |
| 5,374,253 | A | 12/1994 | Burns, Sr. et al. |
| 5,390,585 | A | 2/1995 | Ryuh |
| 5,392,765 | A | 2/1995 | Muller |
| 5,395,313 | A | 3/1995 | Naves et al. |
| 5,403,276 | A | 4/1995 | Schechter et al. |
| 5,409,013 | A | 4/1995 | Clement |
| 5,411,513 | A | 5/1995 | Ireland et al. |
| 5,425,376 | A | 6/1995 | Banys et al. |
| 5,429,601 | A | 7/1995 | Conley et al. |
| 5,443,476 | A | 8/1995 | Shapiro |
| 5,449,356 | A | 9/1995 | Walbrink et al. |
| 5,456,689 | A | 10/1995 | Kresch et al. |
| 5,490,819 | A | 2/1996 | Nicholas et al. |
| 5,490,860 | A | 2/1996 | Middle et al. |
| 5,492,537 | A | 2/1996 | Vancaillie |
| 5,498,258 | A | 3/1996 | Hakky et al. |
| 5,527,331 | A | 6/1996 | Kresch et al. |
| 5,549,541 | A | 8/1996 | Muller |
| 5,556,378 | A | 9/1996 | Storz et al. |
| 5,563,481 | A | 10/1996 | Krause |
| 5,569,164 | A | 10/1996 | Lurz |
| 5,569,254 | A | 10/1996 | Carlson et al. |
| 5,569,284 | A | 10/1996 | Young et al. |
| 5,591,187 | A | 1/1997 | Dekel |
| 5,601,583 | A | 2/1997 | Donahue et al. |
| 5,601,603 | A | 2/1997 | Illi |
| 5,602,449 | A | 2/1997 | Krause et al. |
| 5,603,332 | A | 2/1997 | O'Connor |
| 5,630,798 | A | 5/1997 | Beiser et al. |
| 5,649,547 | A | 7/1997 | Ritchart et al. |
| 5,669,927 | A | 9/1997 | Boebel et al. |
| 5,672,945 | A | 9/1997 | Krause |
| 5,674,179 | A | 10/1997 | Bonnet et al. |
| 5,676,497 | A | 10/1997 | Kim |
| 5,695,448 | A | 12/1997 | Kimura et al. |
| 5,702,420 | A | 12/1997 | Sterling et al. |
| 5,709,698 | A | 1/1998 | Adams et al. |
| 5,730,752 | A * | 3/1998 | Alden et al. .................. 606/180 |
| 5,733,298 | A | 3/1998 | Berman et al. |
| 5,741,286 | A | 4/1998 | Recuset |
| 5,741,287 | A | 4/1998 | Alden et al. |
| 5,749,885 | A | 5/1998 | Sjostrom et al. |
| 5,749,889 | A | 5/1998 | Bacich et al. |
| 5,759,185 | A | 6/1998 | Grinberg |
| 5,772,634 | A | 6/1998 | Atkinson |
| 5,775,333 | A | 7/1998 | Burbank et al. |
| 5,782,849 | A | 7/1998 | Miller |
| 5,807,240 | A | 9/1998 | Muller et al. |
| 5,807,282 | A | 9/1998 | Fowler |
| 5,810,861 | A | 9/1998 | Gaber |
| 5,814,009 | A | 9/1998 | Wheatman |
| 5,833,643 | A | 11/1998 | Ross et al. |
| 5,840,060 | A | 11/1998 | Beiser et al. |
| 5,857,995 | A | 1/1999 | Thomas et al. |
| 5,873,886 | A | 2/1999 | Larsen et al. |
| 5,899,915 | A | 5/1999 | Saadat |
| 5,911,699 | A | 6/1999 | Anis et al. |
| 5,911,722 | A | 6/1999 | Adler et al. |
| 5,913,867 | A | 6/1999 | Dion |
| 5,916,229 | A | 6/1999 | Evans |
| 5,925,055 | A | 7/1999 | Adrian et al. |
| 5,928,163 | A | 7/1999 | Roberts et al. |
| 5,944,668 | A | 8/1999 | Vancaillie et al. |
| 5,947,990 | A | 9/1999 | Smith |
| 5,951,490 | A | 9/1999 | Fowler |
| 5,956,130 | A | 9/1999 | Vancaillie et al. |
| 5,957,832 | A | 9/1999 | Taylor et al. |
| 6,001,116 | A | 12/1999 | Heisler et al. |
| 6,004,320 | A | 12/1999 | Casscells et al. |
| 6,007,513 | A | 12/1999 | Anis et al. |
| 6,024,751 | A | 2/2000 | Lovato et al. |
| 6,032,673 | A | 3/2000 | Savage et al. |
| 6,039,748 | A | 3/2000 | Savage et al. |

(56) References Cited

U.S. PATENT DOCUMENTS

| | | |
|---|---|---|
| 6,042,552 A | 3/2000 | Cornier |
| 6,068,641 A | 5/2000 | Varsseveld |
| 6,086,542 A | 7/2000 | Glowa et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner et al. |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,315,714 B1 * | 11/2001 | Akiba ............... 600/114 |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,773 B1 | 3/2004 | Viola |
| 6,837,847 B2 * | 1/2005 | Ewers et al. ............. 600/114 |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,061,359 B2 | 11/2011 | Emanuel |
| 2001/0039963 A1 | 11/2001 | Spear et al. |
| 2001/0047183 A1 | 11/2001 | Privitera et al. |
| 2002/0058859 A1 | 5/2002 | Brommersma |
| 2002/0165427 A1 | 11/2002 | Yachia et al. |
| 2003/0050603 A1 | 3/2003 | Todd |
| 2003/0050638 A1 | 3/2003 | Yachia et al. |
| 2003/0078609 A1 | 4/2003 | Finlay et al. |
| 2003/0114875 A1 | 6/2003 | Sjostrom |
| 2005/0043690 A1 | 2/2005 | Todd |
| 2005/0085692 A1 | 4/2005 | Kiehn et al. |
| 2006/0036132 A1 | 2/2006 | Renner et al. |
| 2006/0047185 A1 | 3/2006 | Shener et al. |
| 2006/0241586 A1 | 10/2006 | Wilk |
| 2008/0015621 A1 | 1/2008 | Emanuel |
| 2008/0058588 A1 | 3/2008 | Emanuel |
| 2008/0058842 A1 | 3/2008 | Emanuel |
| 2008/0097468 A1 | 4/2008 | Adams et al. |
| 2008/0097469 A1 | 4/2008 | Gruber et al. |
| 2008/0097470 A1 | 4/2008 | Gruber et al. |
| 2008/0097471 A1 | 4/2008 | Adams et al. |
| 2008/0135053 A1 | 6/2008 | Gruber et al. |
| 2008/0146872 A1 | 6/2008 | Gruber et al. |
| 2008/0146873 A1 | 6/2008 | Adams et al. |
| 2008/0245371 A1 | 10/2008 | Gruber |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262308 A1 | 10/2008 | Prestezog et al. |
| 2009/0270812 A1 | 10/2009 | Litscher et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0087798 A1 | 4/2010 | Adams et al. |
| 2010/0152647 A1 | 6/2010 | Shener et al. |

FOREIGN PATENT DOCUMENTS

| | | | |
|---|---|---|---|
| DE | 3601453 A1 | 9/1986 | |
| DE | 3615694 A1 | 11/1987 | |
| DE | 4038398 A1 | 6/1992 | |
| DE | 4440035 A1 | 5/1996 | |
| DE | 19633124 A1 | 5/1997 | |
| DE | 102006022827 | 12/2006 | ............... A61B 1/00 |
| DE | 102006022827 A1 | 12/2006 | |
| EP | 0310285 A2 | 4/1989 | |
| EP | 0557044 A1 | 8/1993 | |
| EP | 0582295 A2 | 2/1994 | |
| EP | 0606531 A2 | 7/1994 | |
| EP | 0621008 A2 | 10/1994 | |
| EP | 0806183 A1 | 5/1997 | |
| EP | 1681022 A1 | 7/2006 | |
| GB | 2093353 A | 9/1982 | |
| GB | 2311468 A | 10/1997 | |
| JP | 01-75416 | 5/1989 | |
| JP | 2002-538889 | 11/2002 | |
| JP | 2003245247 A | 9/2003 | |
| NL | 1006944 C2 | 3/1999 | |
| WO | WO 81/01648 A1 | 6/1981 | |
| WO | WO 92/11816 A2 | 7/1992 | |
| WO | WO 93/07821 A1 | 4/1993 | |
| WO | WO 93/15664 A1 | 8/1993 | |
| WO | WO 94/26181 A1 | 11/1994 | |
| WO | WO 95/05777 A1 | 3/1995 | |
| WO | WO 95/10981 A1 | 4/1995 | |
| WO | WO 95/10982 A1 | 4/1995 | |
| WO | WO 95/22935 A1 | 8/1995 | |
| WO | WO 95/30377 A1 | 11/1995 | |
| WO | WO 96/11638 A1 | 4/1996 | |
| WO | WO 96/26676 A1 | 9/1996 | |
| WO | WO 97/09922 A1 | 3/1997 | |
| WO | WO 97/17027 A1 | 5/1997 | |
| WO | WO 97/19642 A1 | 6/1997 | |
| WO | WO 97/24071 A1 | 7/1997 | |
| WO | WO 97/34534 A1 | 9/1997 | |
| WO | WO 97/35522 A1 | 10/1997 | |
| WO | WO 98/09569 A1 | 3/1998 | |
| WO | WO 98/10707 A1 | 3/1998 | |
| WO | WO 98/46147 A1 | 10/1998 | |
| WO | WO 99/03407 A1 | 1/1999 | |
| WO | WO 99/03409 A1 | 1/1999 | |
| WO | WO 99/07295 A1 | 2/1999 | |
| WO | WO 99/11184 A1 | 3/1999 | |
| WO | WO 99/39648 A1 | 8/1999 | |
| WO | WO 99/44506 A1 | 9/1999 | |
| WO | WO 99/60935 A1 | 12/1999 | |
| WO | WO 00/12010 A1 | 3/2000 | |
| WO | WO 00/28890 A1 | 5/2000 | |
| WO | WO 00/33743 A1 | 6/2000 | |
| WO | WO 00/44295 A1 | 8/2000 | |
| WO | WO 00/47116 A1 | 8/2000 | |
| WO | WO 00/57797 A1 | 10/2000 | |
| WO | WO 01/35831 A1 | 5/2001 | |
| WO | WO 01/58368 A1 | 8/2001 | |
| WO | WO 01/95810 A2 | 12/2001 | |
| WO | WO 02/069808 A2 | 9/2002 | |
| WO | WO 03/022164 A1 | 3/2003 | |
| WO | WO 03/077767 A1 | 9/2003 | |
| WO | WO 2005/060842 A1 | 7/2005 | |
| WO | WO 2005/096963 A2 | 10/2005 | |
| WO | WO 2006/105283 A2 | 10/2006 | |
| WO | WO 2006/121968 A2 | 11/2006 | |
| WO | WO 2006/121970 A2 | 11/2006 | |
| WO | WO 2007/044833 A2 | 4/2007 | |

OTHER PUBLICATIONS

ACMI Corporation, "Dolphin II Hysteroscopic Fluid Management Systems," ACMI Corporation, 2002 (1 page).

ACMI Corporation, "DOLPHIN II and DESTIN-U-FLO Fluid Management Systems for Hysteroscopy", ACMI Corporation, 2002 (1 page).

(56) References Cited

OTHER PUBLICATIONS

Action Closing Prosecution for 95/002,058 mailed Aug. 9, 2013 (34 pages).
Advisory Action in U.S. Appl. No. 11/929,940 mailed Sep. 10, 2010 (3 pages).
Bacsko "Uterine Surgery by Operative Hysteroscopy", European Journal of Obstetrics & Gynecology and Reproductive Biology, vol. 71, pp. 219-222, 1997 (4 pages).
Baggish et al., "Diagnostic and Operative Hysterectomy," Mosby, pp. 97-105, 123-125, 127-132, 353-355, and 394-398, 1999 (27 pages).
Claim chart for anticipation of claims 1-8 based on Banko US 3,945,375 (4 pages).
Claim chart for anticipation of claims 1-8 based on Kresch US 5,456,689 (4 pages).
Claim chart for anticipation of claims 1-8 based on Savage US 6,032,673 (13 pages).
C.R. Bard, Inc, "The HydroFlex HD System" (1 page).
Cravello et al., "Hysteroscopic Resection of Fibroids: Results with a 6-Year Follow-up Period", Journal of Gynecologic Surgery, vol. 15, No. 1, 1-5 1999 (5 pages).
Defendant Hologic Inc.'s Preliminary, Non-Binding List of Asserted Prior Art References in *Smith & Nephew, Inc.* v. *Hologic, Inc.* Civil Action Nos. 11-CV-12064-RWZ and 10-CV-10951-RWZ, U.S. District Court for the District of Massachusetts, Feb. 8, 2012, (7 pages).
Denial of Order for 95/001,955 mailed Jun. 4, 2012 (5 pages).
Denial of Petition for 95/001,955 mailed Sep. 28, 2012 (5 pages).
Dictionary definition of reciprocate, Merrian-Webster Dictionary, on-line edition, retrieved Mar. 20, 2013 (1 page).
Dictionary definition of rotate, Merriam-Webster Dictionary, on-line edition, retrieved Mar. 20, 2013 (1 page).
Dictionary definition of translate, Merriam-Webster Dictionary, on-line edition, retrieved Mar. 20, 2013 (1 page).
Drews et al., "Surgical Approach to Myomas: Laparoscopy and Hysteroscopy", Seminars in Reproductive Endocrinology, vol. 10, No. 4, pp. 367-377, 1992 (11 pages).
Dumesic et al., "A New Approach to Hysteroscopic Cannulation of the Fallopian Tube", Journal of Gynecologic Surgery, vol. 7, No. 1, pp. 7-9, 1991 (3 pages).
Emanuel et al., "Long-term Results of Hysteroscopic Myomectomy for Abnormal Uterine Bleeding", Obstetrics & Gynecoogy, vol. 93, No. 5, Part I, pp. 743-748, 1999 (6 pages).
European Patent Office Examination Report for Application No. 05 786 521.4-2305 dated Apr. 21, 2010 (4 pages).
European Patent Office Examination Report for Application No. 05 786 521.4-2305 dated Sep. 26, 2010 (5 pages).
Executed Expert Declaration of Dr. Henry A. Dominicis in support of Request for Inter Parties Reexamination of U.S. Patent No. 8,061,359, (150 pages).
Executed Expert Declaration of Hal Walbrink in support of Request for Inter Parties Reexamination of U.S. Patent No. 8,061,359 (22 pages).
Exhibit P to Hologic's Opposition to Smith & Nephew's Motion for Preliminary Injunction, Redacted, *Smith & Nephew, Inc.* v. *Hologic, Inc.* Civil Action No. 11-CV-12064-RWZ, filed Dec. 30, 2011 (99 pages).
First Office Action for 95/002,058 mailed Sep. 19, 2012 (37 pages).
Franchini et al., "Endometrial resection: a diagnostic tool in postmenopausal women", Gynecological Endoscopy, 8, pp. 111-114, 1999 (5 pages).
"From Distention to Deficit Monitoring Taking the All-In-One Approach", W.O.M. World of Medicine (1 page).
Gerber et al., "The Endoscapel: A new endoscopic instrument for supracervical hysterectomy and morcellation of masses; clinical evaluation", European Journal of Obstetrics & Gynecology and Reproductive Biology, 86, p. S12, 1999 (1 page).
Gynecare, "Fluid Management System" Instructions for Use (26 pages).
Gynecare "Motor Drive Unit" Instructions for Use (3 pages).
Gynecare X-Tract, "Tissue Morcellator", Instructions for Use (3 pages).

Gynescope Corporation "Laser Fiber Director", Advertisement, Journal of Gynecologic Surgery, vol. 6, No. 1, 1990 (2 pages).
Hess et al., "Textbook of Bilio-Pancreatic Disease", vol. III, PICCIN, e.g. Fig 6.5.1, pp. 1584-1586, 1997 (5 pages).
Hologic's Opposition to Smith & Nephew's Motion for Preliminary Injunction, Redacted, *Smith & Nephew, Inc.* v. *Hologic, Inc.*, Civil Action No. 11-CV-12064-RWZ, filed Dec. 30, 2011 (26 pages).
"HysteRo-Purator 1143-1 Technical Data" WISAP (2 pages).
International Search Report for International Application No. PCT/US2011/053753 mailed on Dec. 20, 2011 (4 pages).
International Search Report for International Application No. PCT/US2005/029807 mailed on Jun. 13, 2006 (5 pages).
Japanese Office Action in Japanese Patent Application No. 2007-530014, dated Feb. 15, 2011 (10 pages).
Karl Storz, Advertisement, Journal of Gynecologic Surgery, vol. 5, No. 4, 1989 (3 pages).
Karl Storz, "Pilot a Course to Successful Outcomes", Intermetro Industries Corporation, 2001 (2 pages).
Karl Storz "Uterine Resectoscopes for Endometrial Ablation and Resection", Advertisement, Journal of Gynecologic Surgery, vol. 6, No. 1, 1990 (3 pages).
Lin et al. "Clinical Applications of a New Fujinon Operating Fiberoptic Hysteroscope", Journal of Gynecologic Surgery, vol. 6, No. 2, pp. 81-87, 1990 (7 pages).
Mettler et al., "Pelviscopic uterine surgery" Surgical Endoscopy, 6, pp. 23-31, 1992 (9 pages).
Neis et al., "Hysteroscopy: Textbook and Atlas", Thieme Medical Publishers, pp. 91-103, 1994 (13 pages).
Nisolle et al., "Endometrial ablation with the Nd-YAG laser in dysfunctional bleeding" Minimally Invasive Therapy, vol. 1, pp. 35-39, 1991 (5 pages).
Office Action in U.S. Appl. No. 09/486,977 mailed Sep. 7, 2005 (7 pages).
Office Action in U.S. Appl. No. 11/780,759 mailed Jul. 22, 2010 (5 pages).
Office Action in U.S. Appl. No. 11/780,759 mailed Jul. 26, 2010 (7 pages).
Office Action in U.S. Appl. No. 11/780,759 mailed Jan. 5, 2011 (7 pages).
Office Action in U.S. Appl. No. 11/929,938 mailed Jul. 30, 2010 (10 pages).
Office Action in U.S. Appl. No. 11/929,938 mailed Jan. 5, 2011 (10 pages).
Office Action in U.S. Appl. No. 11/929,940 mailed Dec. 30, 2009 (9 pages).
Office Action in U.S. Appl. No. 11/929,940 mailed Jul. 1, 2010 (12 pages).
Office Action in U.S. Appl. No. 95/001,933 mailed Jun. 5, 2012 (37 pages).
Office Action in U.S. Appl. No. 95/001,933 mailed Apr. 1, 2013 (94 pages).
Office Action in U.S. Appl. No. 95/001,933 mailed Sep. 19, 2013 (79 pages).
Opening Claim Construction Brief of Defendant Hologic, Inc., from Massachusetts Civil Action No. 1:11-cv-12064-RWZ (Defendant's Opening Markman Brief.) (24 pages).
Opening Markman Brief of Plaintiff Smith & Nephew, Inc., from Massachusetts Civil Action No. 1:11-cv-12064-RWZ "Plaintiff's Opening Markman Brief") (24 pages).
Order Granting Request for Reexam 95/001,933, mailed Jun. 5, 2012 (29 pages).
Park et al., "Endoscopic Management of Uterine Myoma", Yonsei Medical Journal, vol. 40, No. 6, pp. 583-588, 1999 (6 pages).
Patent Owner's Aug. 3, 2012 Response to Office Action for U.S. Appl. No. 95/001,933 mailed Jun. 5, 2012 (151 pages).
Patent Owner's Jun. 3, 2013 Response to Office Action for U.S. Appl. No. 95/001,933 mailed Apr. 1, 2013 (75 pages).
Patent Owner's Oct. 21, 2013 Response to Action Closing Prosecution in 95/001,933 mailed Sep. 19, 2013 (218 pages).
Patent Owner's Jan. 22, 2013 Response to Office Action for 95/002,058 mailed Sep. 9, 2012 (379 pages).
Patent Owner's Sep. 9, 2013 Response to Action Closing Prosecution for 95/002,058 dated Aug. 9, 2013 (7 pages).

(56) References Cited

OTHER PUBLICATIONS

Patent Owner's Oct. 25, 2010 Response to Office Action for U.S. Appl. No. 11/780,759 mailed Jul. 26, 2010 (13 pages).
Patent Owner's Mar. 31, 2011 Response to Office Action for U.S. Appl. No. 11/780,759 mailed Jan. 5, 2010 (15 pages).
PCT International Preliminary Report on Patentability for Application No. PCT/US2005/029807 dated Feb. 28, 2007, (9 pages).
Petition for Review for 95/001,955, Jul. 3, 2012 (36 pages).
Reexam Order for 95/002,058 mailed Sep. 19, 2012 (54 pages).
Reexamination Litigation Search Report CRU 3999 filed Apr. 2, 2012 in U.S. Appl. No. 95/001,955 (33 pages).
Reference AQ "Fishing Reel produced and sold by Shimano of Japan in to the U.S. prior to Oct. 26, 2001," filed Oct. 17, 2005 in the prosecution file history of U.S. Appl. No. 09/983,810 (7 pages).
Request for Inter Partes Reexamination of U.S. Patent No. 8,061,359, filed Apr. 2, 2012 (265 pages).
Richard Wolf "Morce- Power 2306" Electronic Morcellator (2 pages).
Richard Wolf "The Fluid Manager" (2 pages).
Right of Appeal Notice mailed Jan. 14, 2014 for U.S. Appl. No. 95/001,933 (58 pages).
Second Office Action for 95/002,058 mailed Jan. 24, 2014 (31 pages).
Sheath et al., "Fiberoptic Light for Oophorectomy at Vaginal Hysterectomy", Journal of Gynecologic Surgery, vol. 14, No. 3, pp. 119-22, 1998 (4 pages).
Sugimoto "A Color Atlas of Hysteroscopy" Springer-Verlag Tokyo, 1999 (17 pages).

Third Party Response to Office Action for U.S. Appl. No. 95/001,933 mailed Apr. 1, 2013 (101 pages).
Third Party Response to Office Action for U.S. Appl. No. 95/001,933 mailed Jun. 5, 2012 (777 pages).
Third Party Response in U.S. Appl. No. 95/001,933 to Action Closing Prosecution mailed Sep. 19, 2013 (38 pages).
Third Party Response to First Office Action for 95/002,058 mailed on Sep. 19, 2012.
Third Party Response in 95/002,058 to Action Closing Prosecution mailed Apr. 1, 2013 (101 pages).
Third Party Response in 95/002,058 to Action Closing Prosecution mailed Aug. 9, 2013 (25 pages).
Valle "Hysteroscopic Removal of Submucous Leiomyomas", Journal of Gynecologic Surgery, vol. 6, No. 1, pp. 89-96, 1990 (9 pages).
Weck "A Direct Path to Diagnostic and Operative Control: The Weck-Baggish Hysteroscopy System" Advertisement, Journal of Gynecologic Surgery, vol. 7, No. 1, 1991 (2 pages).
Williamson et al., Editorial 1 "Complications of hysteroscopic treatments of menorrhagia", British Journal of Anesthesia, vol. 77, No. 3, pp. 305-308, 1996 (4 pages).
European Patent Office Examination Report for Application No. 11 770 261.3-1657 dated Feb. 11, 2014 (4 pages).
PCT International Preliminary Report on Patentability for Application No. PCT/US2011/053753 dated Apr. 2, 2013 (7 pages).
Chinese Office Action for Chinese Application No. 201180046921.6, mailed Dec. 23, 2014, 29 pages, with English language translation.
First Office Action for Japanese Patent Application No. 2013-531779 dated May 18, 2015, with English translation, 6 pages.
Patent Examination Report No. 1 for Australian Patent Application No. 2011308834 dated Jun. 11, 2015, 3 pages.

* cited by examiner

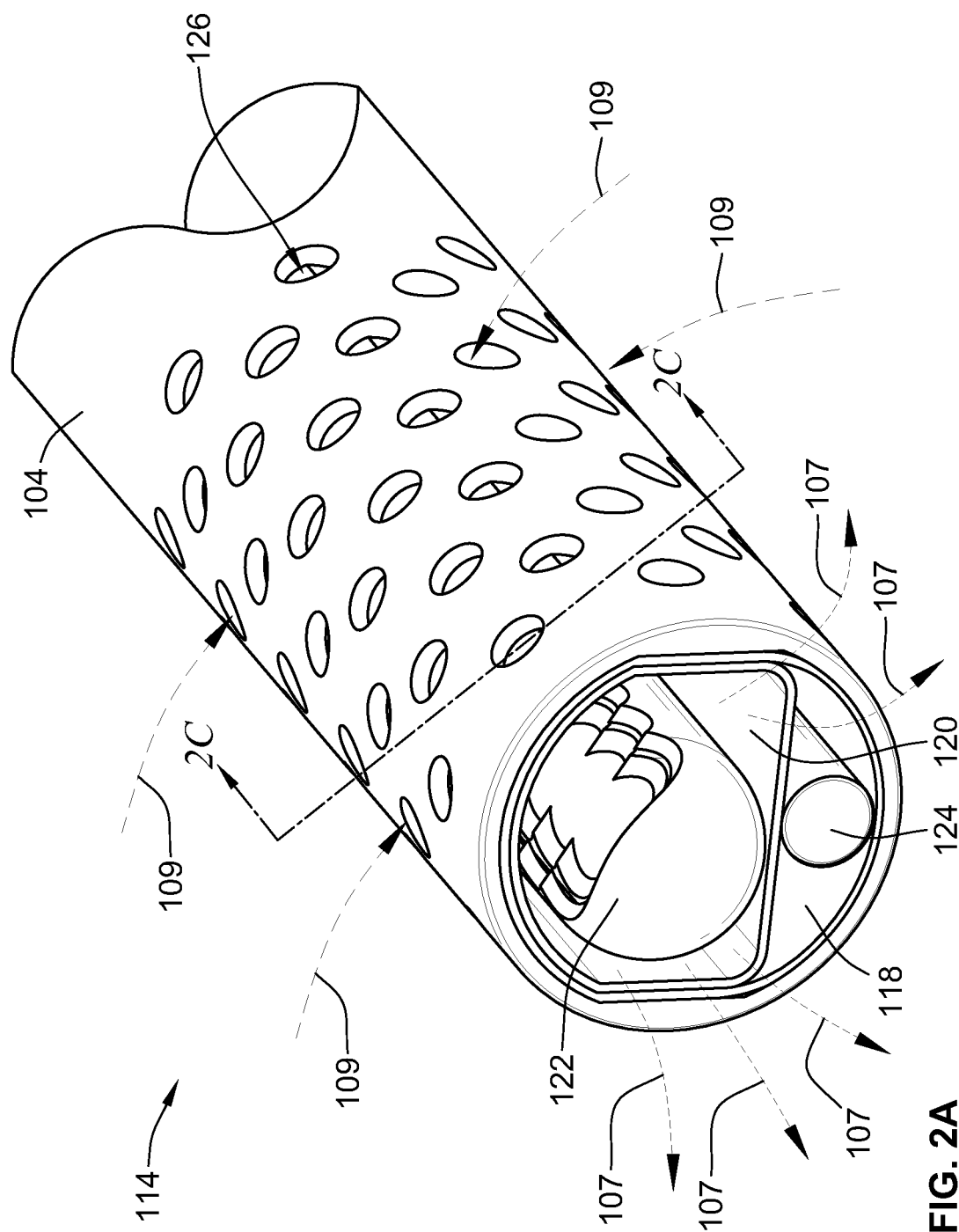

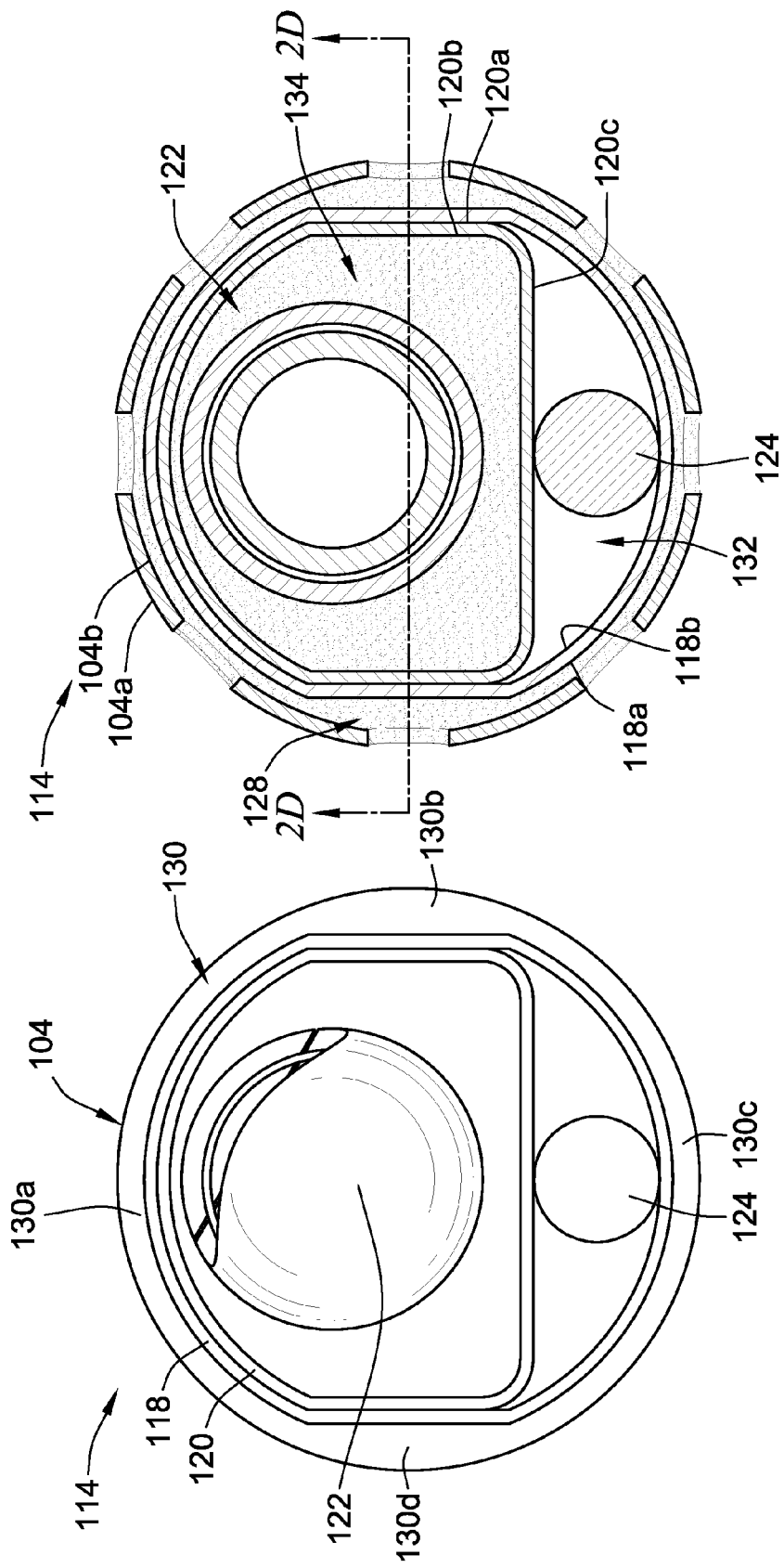

HYSTEROSCOPIC SYSTEM

FIELD OF THE INVENTION

The present invention relates generally to hysteroscopy systems, and, more particularly, to a hysteroscopy system having a small size for use in an office setting.

BACKGROUND OF THE INVENTION

Hysteroscopy refers generally to the inspection of a uterine cavity using a hysteroscope with access through the cervix. As such, hysteroscopy allows diagnosis of intrauterine pathology and, furthermore, can be used for surgical intervention. The hysteroscope typically includes a scope and a sheath.

One problem associated with some current hysteroscopy systems is that they must be used in an operating room setting with the patient being under some type of anesthesia. Anesthesia is required in particular because the size of current hysteroscopes is large and, as such, they can cause discomfort and pain to the patient. For example, a typical hysteroscope may have an outermost diameter of about 9 millimeters. Such hysteroscopes include a scope having a diameter of about 8 millimeters and a sheath having a diameter of about 9 millimeters. In comparison, scientific literature on the subject agrees that hysteroscopy can be performed using a vaginoscopic approach, which can be performed in an office setting, only when the outermost diameter of the hysteroscope is about 6 millimeters or less.

Another problem associated with current scopes is that they typically include a blunt flange at the scope distal end. The flange extends outwardly from the scope and make it difficult, if not impossible, to use the scope without the sheath and/or without an obturator. Accordingly, the size of some current hysteroscopes is limited to the size of the scope and the sheath, .e.g., a diameter of 9 millimeters.

What is needed, therefore, is a hysteroscope system for an office setting that addresses the above-stated and other problems.

SUMMARY OF THE INVENTION

According to one aspect of the present invention, a hysteroscopy system is directed to performing a medical procedure in an office setting. The hysteroscopy system includes a scope having an outer surface, an internal channel defined by an inner surface, and a distal end. A sheath is removably coupled to the scope and has a tip at which a distal flange extends internally towards the outer surface of the scope. The sheath also has an inner surface and a plurality of outflow holes near the distal flange. An outflow channel is formed between the inner surface of the sheath and the outer surface of the scope, the distal flange forming a distal end of the outflow channel. An operative channel is formed within the internal channel of the scope for receiving at least one of a surgical tool and an inflow fluid, and a visualization channel is formed adjacent to the operative channel for receiving a visualization device.

According to yet another aspect of the invention, a hysteroscopy system for a medical procedure includes a scope in the form of an elongated tubular member having an outer surface and an internal surface. The internal surface of the scope defines an internal channel of the scope. A sheath is in the form of an elongated tubular member removably coupled to the scope, the sheath having an outer surface and an internal surface. The sheath has a flange extending internally towards the outer surface of the scope at a distal end of the sheath. An operative member is located within the internal channel of the scope and is in the form of an elongated D-shape tubular member. The operative member has an outer surface and an internal surface, the outer surface being spaced away from the internal surface of the scope to form a visualization channel.

According to yet another aspect of the invention, a hysteroscopy system includes a scope having an outer surface and an internal channel, and a sheath removably coupled to the scope. The sheath has an inner surface and a distal flange, the distal flange extending internally towards the outer surface of the scope. An outflow channel is formed between the inner surface of the sheath and the outer surface of the scope, the distal flange forming a distal end of the outflow channel between the scope and the sheath.

Additional aspects of the invention will be apparent to those of ordinary skill in the art in view of the detailed description of various embodiments, which is made with reference to the drawings, a brief description of which is provided below.

BRIEF DESCRIPTION OF THE DRAWINGS

FIG. 2A is an enlarged perspective view of a distal end of the hysteroscope system.

FIG. 2B is an enlarged side view of the distal end of the hysteroscope system.

FIG. 2C is an enlarged cross-sectional end view of the distal end of the hysteroscope system.

Figure 1:
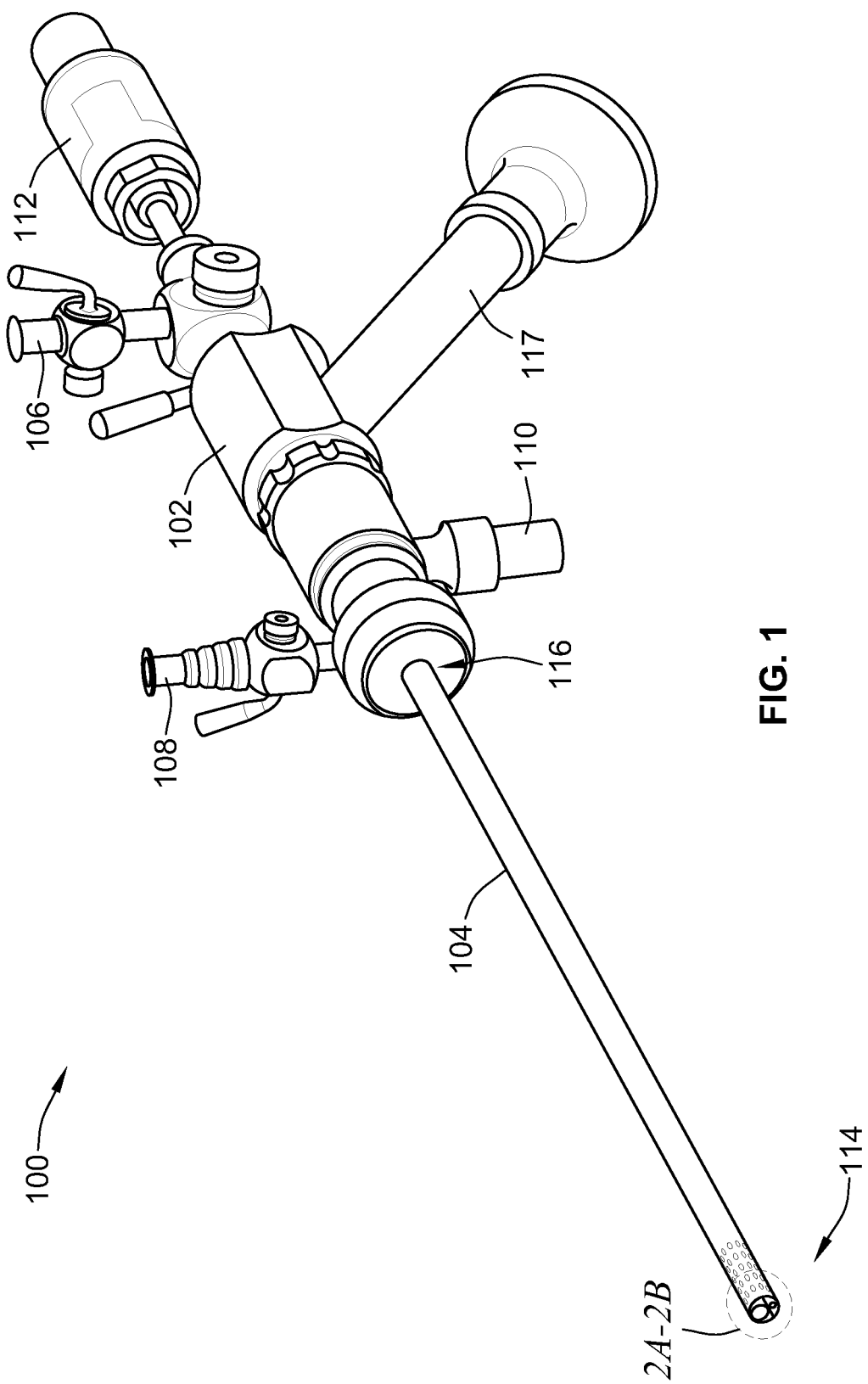
FIG. 1 is a perspective view of a hysteroscope system.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

Referring to FIG. 1, a hysteroscope system 100 includes a hysteroscope 102 having, inter alia, a sheath 104, an inflow valve 106, an outflow valve 108, a light post 110, and a morcellator 112. The sheath 104 is a generally an elongated tubular member that has a distal end 114 and a proximal end 116. The hysteroscope system 100 also includes an arm 117 that is connected to an imaging device (e.g., a camera) to capture images received via a visualization device (e.g., visualization device 124).

According to some exemplary embodiments, the hysteroscope system 100 is intended for morcellation of uterine pathology with a scope and accessories having a sufficiently small diameter that can be inserted into a patient's uterus using the vaginoscopic approach. In particular, the hysteroscope system 100 provides a way to minimize patient pain because a tenanculum and speculum are not typically used.

Furthermore, anesthesia is not needed and the medical procedures can be performed in an office setting. This may result, for example, in a quicker surgery with less pain and quicker recovery, and may potentially lower the cost of the surgery. Yet another advantage of the hysteroscope system 100 is that a surgeon has the option to decide if they prefer greater flow instruments (e.g., with a coupled sheath 104) or smaller diameter instruments (e.g., with a removed sheath 104), depending on the patient case.

Referring to FIG. 2A, the sheath 104 is removably coupled to a scope 118, which is generally an elongated tubular member having (similar to the sheath 104) a distal end 114 and a proximal end 116. More specifically, the sheath 104 is slidably fitted in an overlapping manner over the scope 118. The scope 118 includes an operative member 120, which is in the form of an elongated D-shape tubular member.

The operative member 120 receives internally a surgical tool 122, which can be selected from a variety of different tools. For example, the surgical tool 122 can be a rotary morcellator, a reciprocating morcellator, or a morcellator having both reciprocal and rotary capabilities. The scope 118 further includes a visualization device 124. The visualization device 124 is adjacent to the operative member 120 and can include various image devices. For example, the visualization device 124 can include fiber-optic technology for illumination and image transmission.

To maintain continuous outflow, a plurality of outflow holes 126 are formed near the distal end 114 of the sheath 104. The inflow valve 106 (shown in FIG. 1) regulates inflow of a liquid through the operative member 120, as represented by the arrows 107 extending from the operative member 120. The liquid is used, for example, to distend and irrigate the uterus of a patient. Furthermore, the liquid is generally received from an access pump, which delivers the fluid to produce a substantially constant predetermined pressure level within a joint cavity, e.g., a uterus. The outflow valve 108 (shown in FIG. 1) regulates outflow of the liquid through the outflow holes 126 via an outflow channel 128 (shown in FIG. 2C) formed between the sheath 104 and the scope 118. The outflow of the liquid is represented by the arrows 109 extending into the outflow holes 126. The outflow liquid is generally sent to a waste container.

Referring to FIG. 2B, the sheath 104 has at the distal end 114 a flange 130 extending inwardly towards the scope 118 to form a closed end of the outflow channel 128 (shown in FIG. 2C). The flange 130 has a generally oval shape and includes two pairs of opposite sides 130a-130d.

According to the illustrated embodiment, the shape of the flange 130 is non-uniform. For example, a second side 130b extends a greater distance internally towards the center of the scope 118 than a first side 130a. Similarly, based on the symmetric features of this embodiment, a fourth side 130d extends a greater distance internally towards the center of the scope 118 than a third side 130c. In alternative embodiments, the flange 130 can have different shapes and sizes.

Figure 2D:
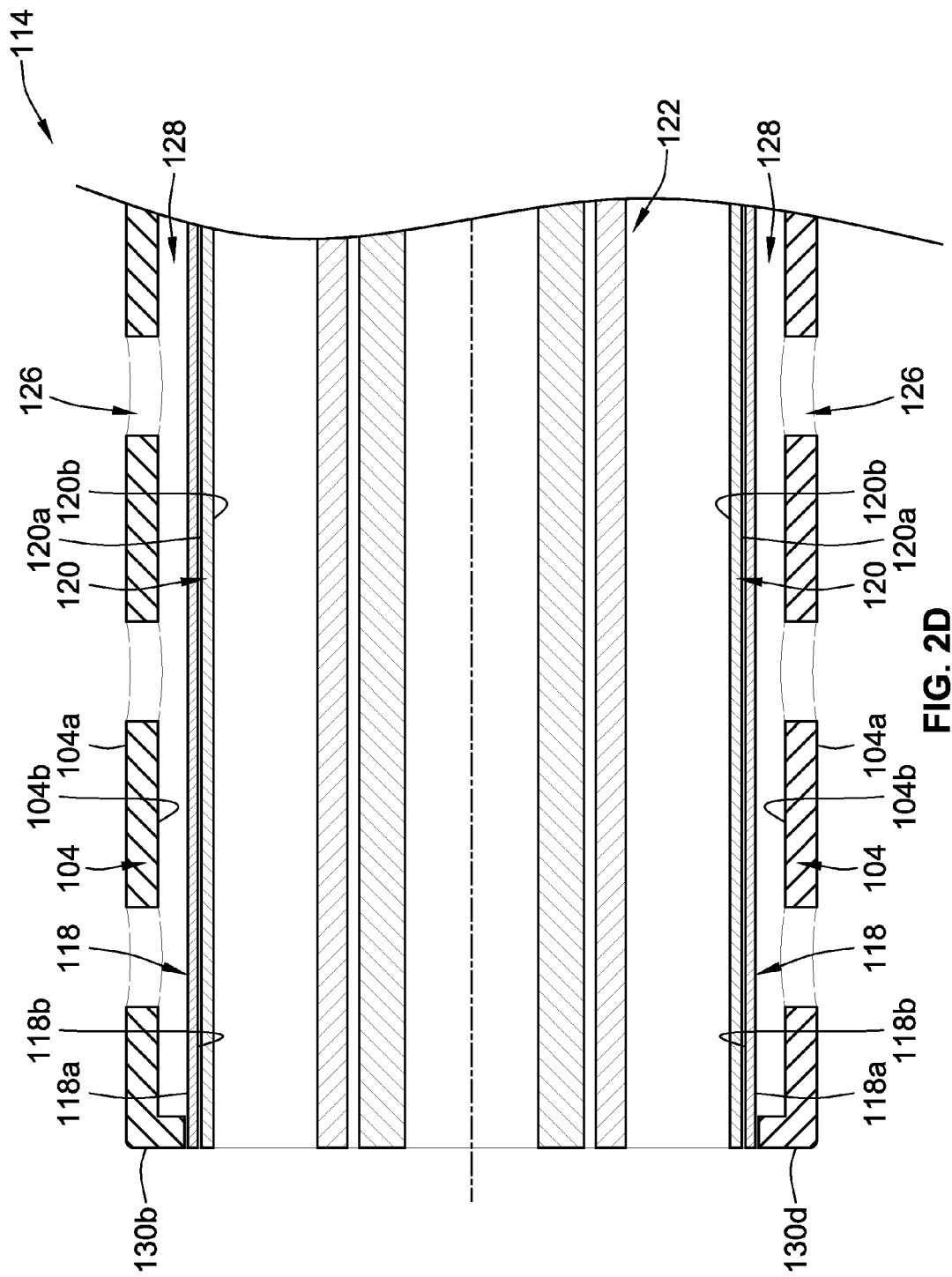
FIG. 2D is an enlarged cross-sectional top view of the distal end of the hysteroscope system.

Referring to FIGS. 2C-2D, the sheath 104 has an outer surface 104a and an internal surface 104b, and the scope 118 has an outer surface 118a and an internal surface 118b. The internal surface 104b of the sheath 104 defines an internal channel in which the scope 118 and the visualization device 124 are located. The internal surface 118b of the scope 118 defines an internal channel in which the outer member and thus the surgical tool 122 is located.

The operative member 120 has an outer surface 120a, an internal surface 120b, and a flat outer surface 120c (clearly shown in FIG. 2C). The flat outer surface 120c is spaced away from the internal surface 118b of the scope 118 to form a visualization channel 132 (clearly shown in FIG. 2C) in which the visualization device 124 is located. The visualization channel 132 is only a small part of the larger internal channel of the scope 118.

The outflow channel 128 is formed between the internal surface 104b of the sheath 104 and the outer surface 118a of the scope 118. An inflow channel 134 is formed in the internal channel of the scope 118. If the surgical tool 122 is removed, the inflow channel 134 is simply the entire internal channel of the scope 118. If the surgical tool 122 is in place, the inflow channel 134 is limited to the area between the surgical tool 122 and the internal surface 120b of the operative member 120.

Figure 3:
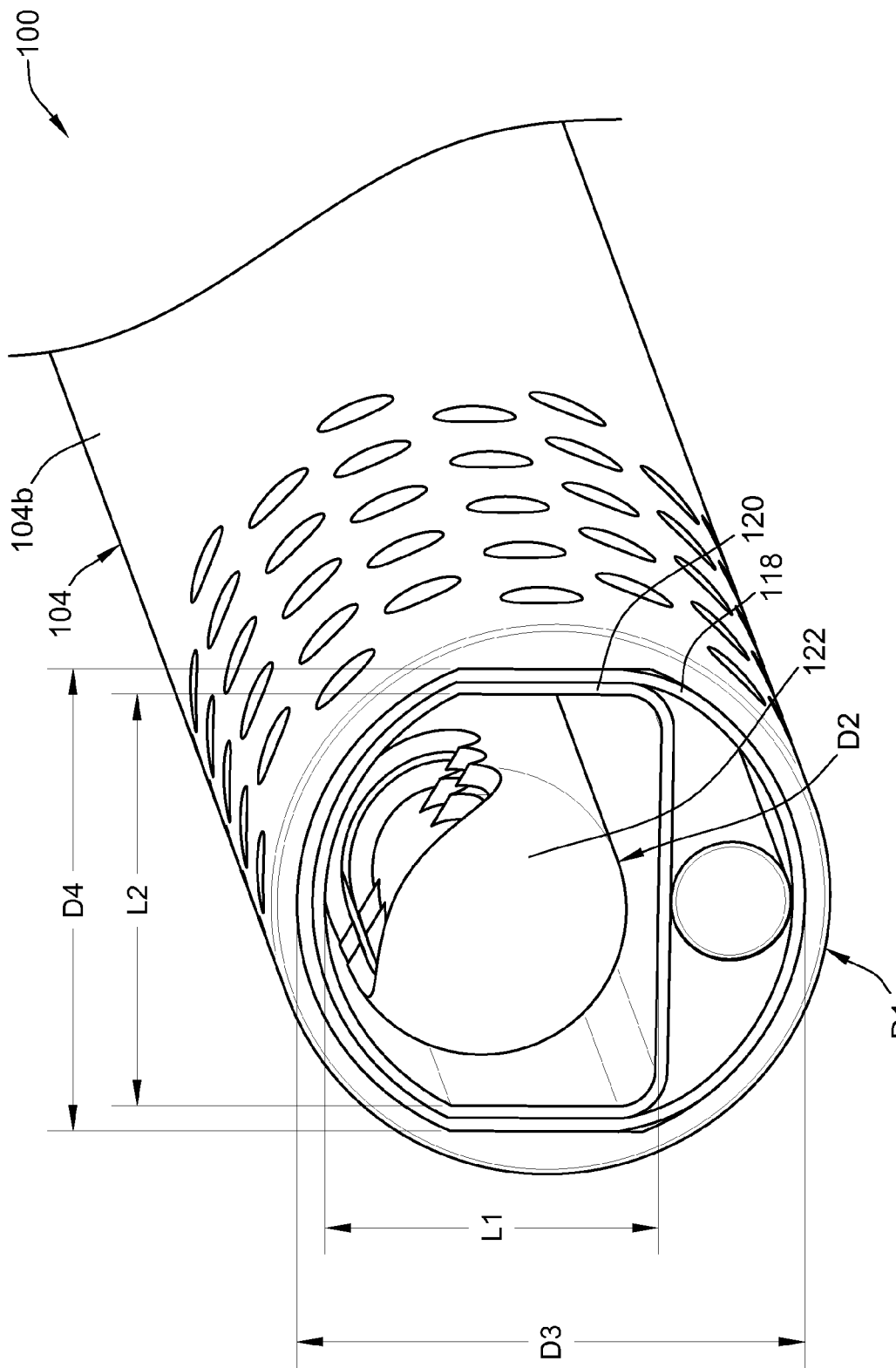
FIG. 3 shows dimensions associated with the distal end of FIG. 2A.

Referring to FIG. 3, the hysteroscopy system 100 is designed to have a size that can be used in an office setting. Specifically, the outer most diameter is designed to be about 6 millimeters or less. According to the illustrated embodiment, the outer diameter D1 of the sheath 104 (which is the same as the diameter of the outer surface 104b) is about 5.6 millimeters. For example, in an alternative embodiment the diameter of the sheath 104 is 5.5 millimeters. The outer diameter D2 of the surgical tool 122 (e.g., morcellator) is about 2.9 millimeters.

The scope 118 has an oval shape with a long diameter D3 of about 5.15 millimeters and a short diameter D4 of about 4.6 millimeters. The operative member 120 has a curvature dimension L1 of about 3.1 millimeters and a flat dimension L2 of about 3.95 millimeters.

The relatively small dimensions of the hysteroscopy system 100 allows a patient to be treated in an office setting. Generally, medical procedures may be provided to a patient with the use of the current hysteroscopy system 100 such that little or no anesthesia may be necessary. Clearly, one advantage of the hysteroscopy system 100 is that it is sufficiently small in diameter to be suitable for the vaginoscopic approach.

Figure 4:
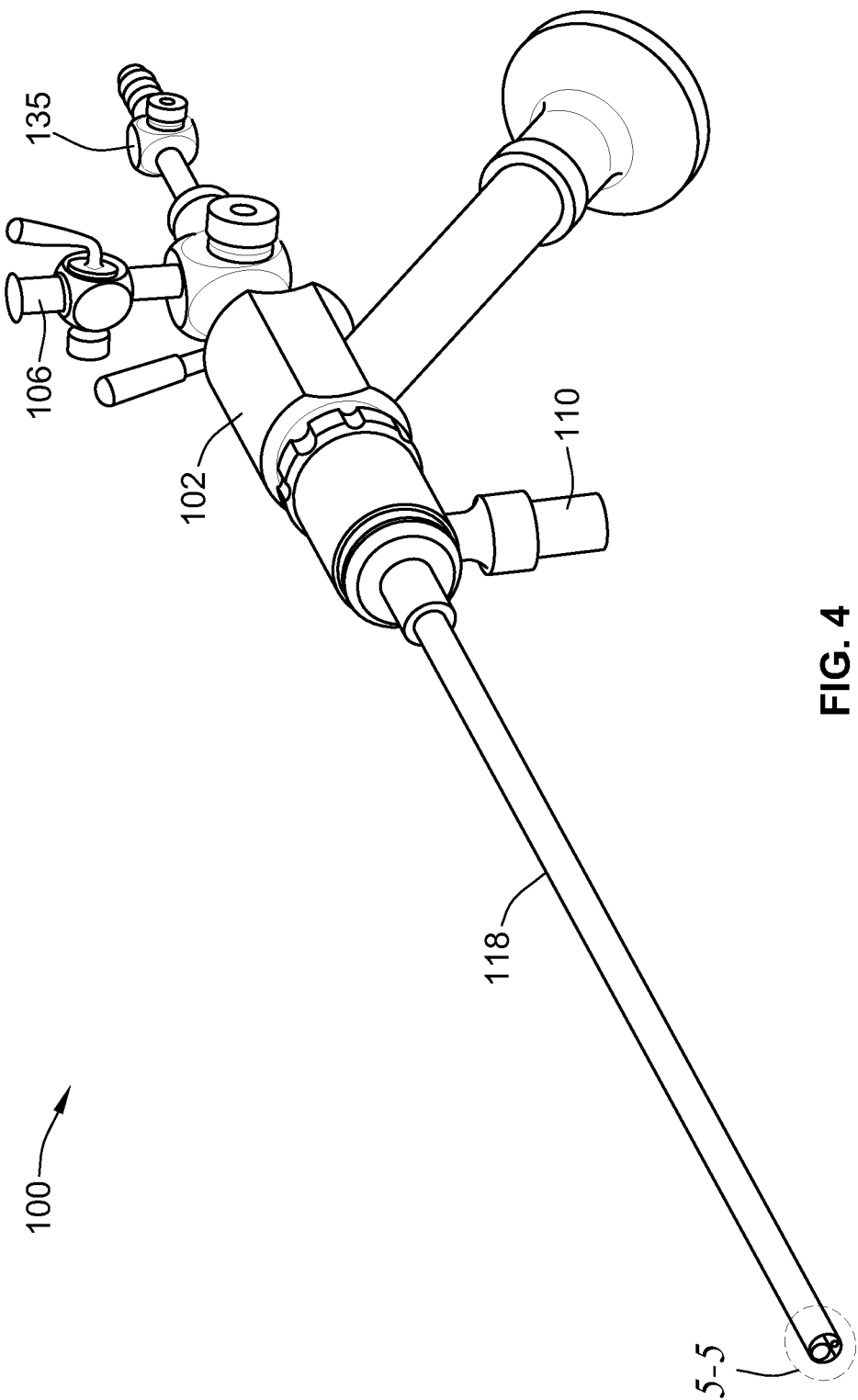
FIG. 4 is a perspective view of the hysteroscope system having a sheath removed from a scope.

Referring to FIG. 4, the hysteroscopy system 100 is also usable without the sheath 104 while still providing continuous flow via a diagnostic cannula 135 (e.g., a cannula having a diameter of about 2.9 millimeters). Specifically, the sheath 104 is removed to allow only the insertion of the scope 118 into a patient, e.g., into an uterus. The removal of the sheath 104 decreases the outermost diameter of the hysteroscopy system 100. For example, in accordance with the dimensions described above in reference to FIG. 3, the outermost diameter decreases to about 5.15 millimeters (the long diameter D3) from about 5.6 millimeters (the outer diameter D1). When the sheath 104 is removed, the outflow can be provided by an operation tool, such as the morcellator 112 described above (shown in FIGS. 1-3), or by the diagnostic cannula 135.

In contrast to previous scopes, the scope 118 does not have a flange extending outwards from its distal end. The outward extending flange of the previous scopes unnecessarily increased the outermost diameter of the respective scopes and created an obtrusive distal end that made it difficult, if not impossible, to introduce into a patient without a sheath and obturator.

Figure 5:
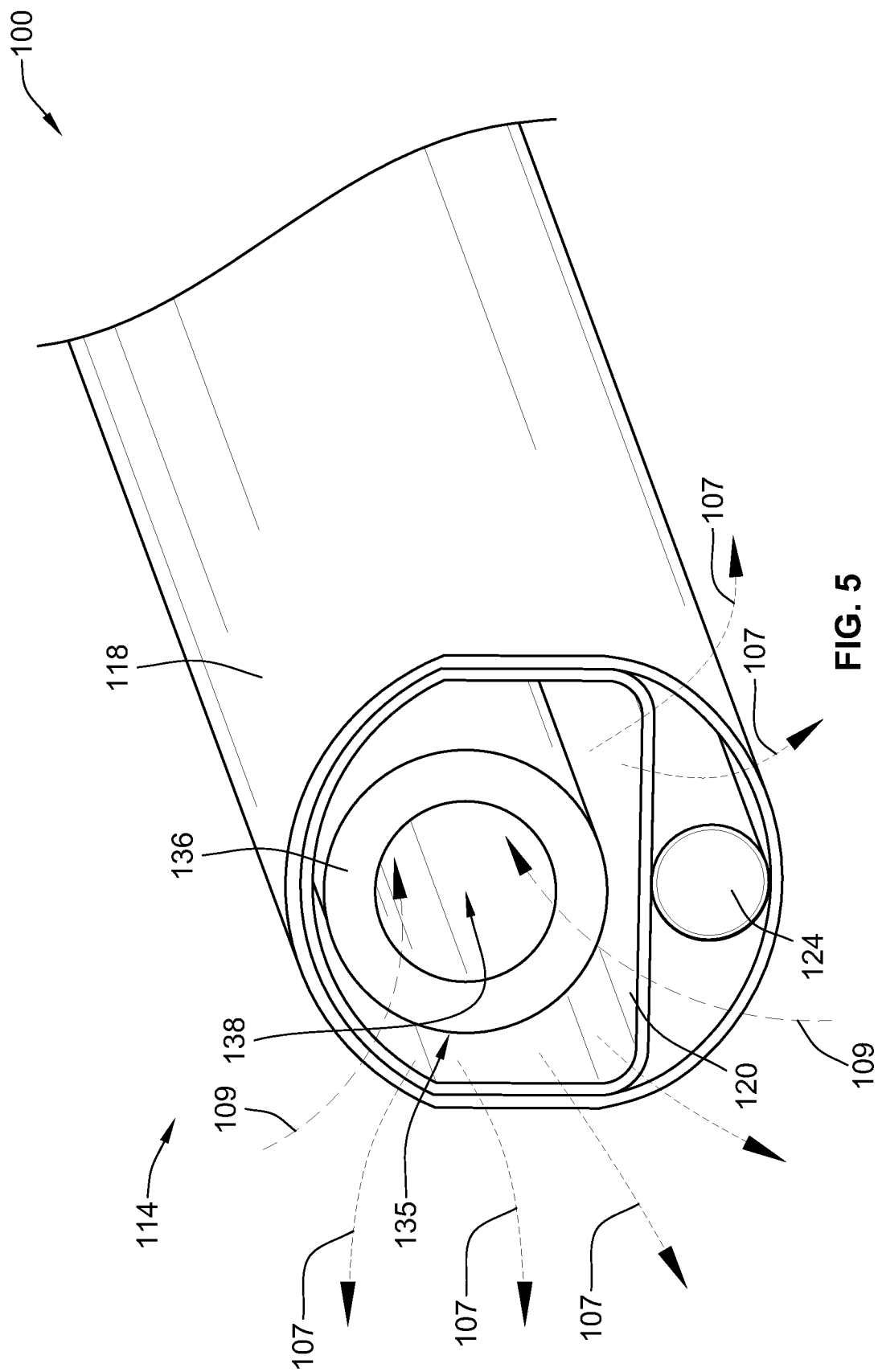
FIG. 5 is an enlarged perspective view of the distal end of the hysteroscope system of FIG. 4.

Referring to FIG. 5, the hysteroscopy system can be used for diagnostic purposes when the sheath 104 is removed. The sheath 104 is likely to be used in operative cases mostly to clear the visual field before introduction of a morcellator blade. The diagnostic cannula 135, which has a distal end 136, is used to create a smaller overall diameter of the system for diagnostic purposes. According to the dimensions described above, a reduction of approximately 0.5 millimeters can be achieved by removing the sheath 104. Another advantage of the cannula 135 is that it can be made reusable.

Yet another advantage of the cannula 135 is that it can be used to distend and irrigate the patient's uterus during the diagnostic procedure.

The cannula 135 allows for continuous outflow but does not extend beyond the distal end of the scope 118. For example, the cannula 135 provides a replacement for the outflow channel 128, which is removed with the removal of the sheath 104. Specifically, the cannula 135 provides an alternative outflow channel 138 to replace the outflow channel 128 formed by the sheath 104. As such, continuous flow can be maintained even if the sheath 104 is removed.

Figure 6:
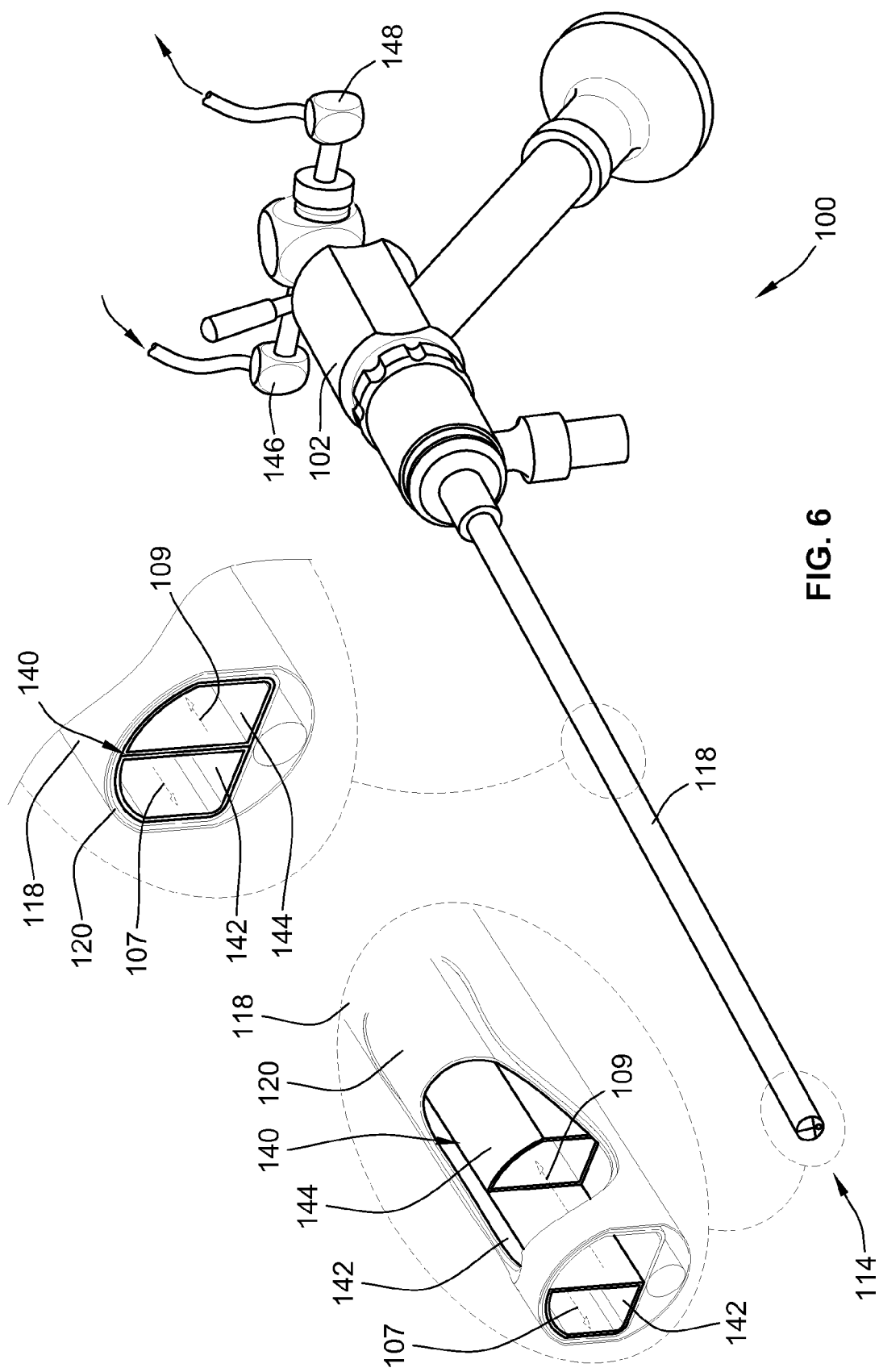
FIG. 6 is a perspective view of an alternative embodiment of the hysteroscope system.

Referring to FIG. 6, the hysteroscope system 100 alternatively includes a flow device 140 inserted within the operative member 120. The flow device 140 has an inflow tubular element 142 and an outflow tubular element 144, which can be conjoined elements or separate elements.

The distal ends of the tubular elements 142, 144 terminate at different points within the operative member 120. Preferably, the distal end of the inflow tubular element 142 terminates at the distal end 114 of the scope 118, and the distal end of the outflow tubular element 144 terminates some distance away from the distal end 114 within the operative member 120. The termination of tubular elements 142, 144 at different points along the operative member 120 eliminates the possibility of fluid short-circuit and provides better circulation and, hence, irrigation within the uterus.

According to one example, the flow device 140 is made of stainless steel and, as such, can be a reusable device. According to another example, the flow device 140 is made from a much more cost-effective material, such as a polymer. If a polymer is used, the flow device 140 will typically be considered a single-use device.

In practice, for example, a surgeon will insert the flow device 140 into the operative member 120 of the hysteroscope 102 prior to introduction into the uterus of a patient. After hysteroscope introduction into the uterus, an inflow valve 146 of the flow device 140 will be opened and the uterus will be distended. Then, by opening an outflow valve 148 of the flow device 140, irrigation is achieved. In the case of a diagnostic procedure, the flow device 140 could stay in place for the duration of the surgery. In the case of an operative procedure, the flow device 140 is removed and an operative tool (e.g., the morcellator 112) is inserted into the scope 118.

While the best modes for carrying out the present invention have been described in detail, those familiar with the art to which this invention relates will recognize various alternative designs and embodiments for practicing the invention within the scope of the appended claims. For example, the sheath 104, the scope 118, and the surgical tool 122 can be circular, oval, or any other smooth shape (i.e., an unobtrusive shape such as a shape that does not have a outward extending flange). In another example, the operative member 120 can have a circular shape or any other similar shape to the illustrated D-shape.

What is claimed is:

1. A hysteroscopy system, the system comprising:
    a scope having an outer surface and an internal channel defined by an inner surface;
    a sheath removably coupled to the scope and having a tip at which a distal flange extends internally in a protruding manner towards the outer surface of the scope, the sheath further having an inner surface;
    an outflow channel formed between the inner surface of the sheath and the outer surface of the scope, the distal flange extending internally in the protruding manner to form a distal end of the outflow channel between the scope and the sheath;
    an operative channel formed within the internal channel of the scope; and
    a visualization channel formed adjacent to the operative channel,
    wherein the distal flange and the sheath are monolithic, a first edge portion of the distal flange facing towards the scope protrudes a first distance towards the outer surface of the scope in a radial direction, a second edge portion of the distal flange facing towards the scope protrudes a second distance towards the outer surface of the scope in the radial direction, and the first distance is different than the second distance.

2. The hysteroscopy system of claim 1, further comprising a surgical tool inserted within the operative channel, the surgical tool being selected from a group consisting of a rotary morcellator, a reciprocating morcellator, or a rotary and reciprocating morcellator.

3. The hysteroscopy system of claim 1, wherein the visualization channel is configured for receiving a visualization device.

4. The hysteroscopy system of claim 1, further comprising an operative member inserted within the scope, the operative member having an outer surface and an internal channel.

5. The hysteroscopy system of claim 4, wherein the outer surface of the operative member has a generally D-shape.

6. The hysteroscopy system of claim 4, further comprising a tool inserted within the internal channel of the operative member.

7. The hysteroscopy system of claim 6, further comprising a fluid flowing through the internal channel of the operative member, the fluid flowing between the tool and the internal channel of the operative member.

8. The hysteroscopy system of claim 1, wherein the sheath has an outer diameter of about 5.6 millimeters and a long diameter of the scope is about 5.15 millimeters.

9. The hysteroscopy system of claim 1, wherein the distal flange extends internally in the protruding manner towards the outer surface of the scope such that an internal diameter of a proximal end of the sheath is greater than an internal diameter of the distal flange.

10. A hysteroscopy system, the system comprising:
    a scope having an outer surface and an inner surface relative to a radial direction of the scope, the inner surface defining an inflow channel and the outer surface being continuous through a distal end of the hysteroscopy system;
    a sheath removably coupled to the scope, the sheath having an outer surface and an inner surface relative to the radial direction, the sheath further having a distal flange protruding from the inner surface of the sheath and towards the outer surface of the scope at the distal end of the hysteroscopy system; and
    an outflow channel formed between the inner surface of the sheath and the outer surface of the scope, the distal flange engaging the outer surface of the scope to form an end of the outflow channel between the scope and the sheath at the distal end of the hysteroscopy system,
    wherein the distal flange and the sheath are monolithic, a first edge portion of the distal flange facing towards the scope protrudes a first distance towards the outer surface of the scope in the radial direction, a second edge portion of the distal flange facing towards the scope protrudes a second distance towards the outer surface of the scope in the radial direction, and the first distance is different than the second distance.

11. The hysteroscopy system of claim 10, wherein the distal flange has an oval shape with a non-uniform diameter.

12. The hysteroscopy system of claim 11, wherein the oval shape has two opposite sides that extend a greater distance internally towards the center of the scope than two other opposite sides.

13. The hysteroscopy system of claim 10, wherein the sheath has an outer diameter of about 5.6 millimeters and a long diameter of the scope is about 5.15 millimeters.

14. The hysteroscopy system of claim 10, wherein the sheath further includes a plurality of outflow holes near the distal flange.

15. The hysteroscopy system of claim 10, further comprising a visualization channel formed within the internal surface of the scope.

16. The hysteroscopy system of claim 15, further comprising a visualization device inserted within the visualization channel.

\* \* \* \* \*